United States Patent [19]

Yamamoto et al.

[11] Patent Number: 4,953,111

[45] Date of Patent: Aug. 28, 1990

[54] DOZE DETECTOR

[75] Inventors: Norihito Yamamoto, Shiga; Takahide Tanaka, Kyoto, both of Japan

[73] Assignee: Omron Tateisi Electronics Co., Kyoto, Japan

[21] Appl. No.: 154,720

[22] Filed: Feb. 11, 1988

[30] Foreign Application Priority Data

| Feb. 12, 1987 | [JP] | Japan | 62-30036 |
| Feb. 13, 1987 | [JP] | Japan | 62-32084 |
| Mar. 4, 1987 | [JP] | Japan | 62-49653 |
| Apr. 15, 1987 | [JP] | Japan | 62-92675 |

[51] Int. Cl.$^5$ ............................................. G08B 23/00
[52] U.S. Cl. .................................. 364/569; 340/575; 340/576
[58] Field of Search .......... 364/569; 340/32 B, 384 R, 340/407, 692, 573 R, 575, 576; 250/336.1, 338.1, 372; 351/209, 210; 180/272; 128/733, 745

[56] References Cited

U.S. PATENT DOCUMENTS

| 3,863,243 | 1/1975 | Skolnick et al. | 250/336 X |
| 4,144,531 | 3/1979 | Anbergen | 340/575 |
| 4,203,098 | 5/1980 | Muncheryan | 340/407 X |
| 4,397,531 | 8/1983 | Lees | 351/210 |
| 4,561,448 | 12/1985 | Buchas | 728/745 X |
| 4,725,824 | 2/1988 | Yoshioka | 340/575 |
| 4,735,498 | 4/1988 | Uddén et al. | 351/210 |

FOREIGN PATENT DOCUMENTS

| 3420043 | 12/1985 | Fed. Rep. of Germany | 340/575 |
| 77986 | 5/1949 | Japan . | |
| 35859 | 11/1970 | Japan . | |
| 33527 | 6/1973 | Japan . | |
| 82096 | 4/1974 | Japan . | |
| 38238 | 3/1975 | Japan . | |
| 66098 | 3/1979 | Japan . | |
| 186538 | 3/1984 | Japan . | |
| 142699 | 11/1984 | Japan . | |
| 592 | 6/1985 | Japan . | |
| 15129 | 2/1987 | Japan . | |
| 1643 | 9/1987 | Japan . | |
| WOA03113 | 5/1986 | PCT Int'l Appl. . | |
| 2133598 | 7/1984 | United Kingdom | 340/575 |

OTHER PUBLICATIONS

Medical & Biological Engineering & Computing, vol. 19, No. 4, Jul. 1981, pp. 509–513, IFMBE, Stevenage, GB; C. R. Genter, II et al.; "Coincidence Eye Position Device with Applications in Clinical Psychophysics, Eye-Position Training and Visual Evoked Response Recording".

Primary Examiner—Parshotam S. Lall
Assistant Examiner—Joseph L. Dixon
Attorney, Agent, or Firm—Wegner & Bretschneider

[57] ABSTRACT

A doze detector detects when the user begins to go to sleep, by detecting the blinks of the user's eye, regardless of the position of the iris, using at least two reflection type sensors. A blink is determined to have occurred only when both light detecting elements detect a blink. The number and/or duration of the blinks is then used to determine whether the user is beginning to doze. An alarm can then be produced to prevent the user from going to sleep.

24 Claims, 13 Drawing Sheets

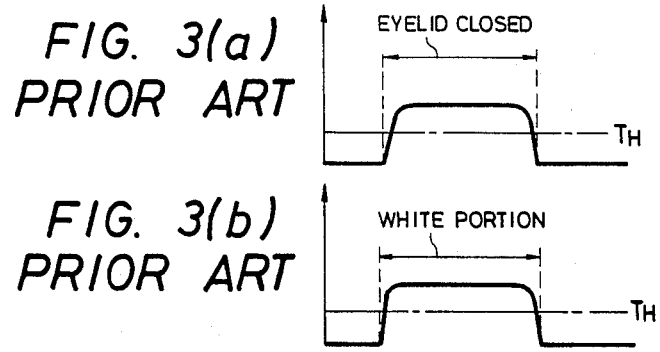
FIG. 3(a) PRIOR ART
FIG. 3(b) PRIOR ART
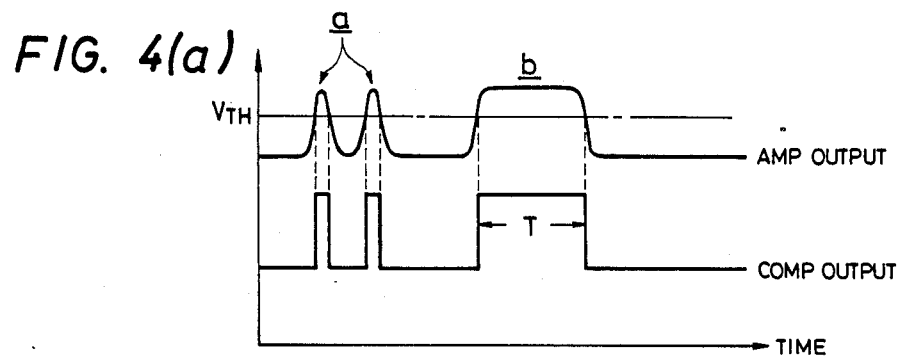
FIG. 4(a)
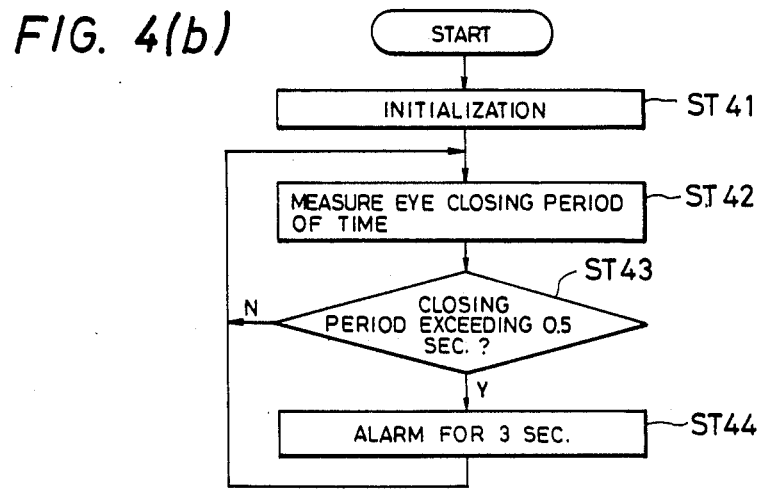
FIG. 4(b)

DOZE DETECTOR

BACKGROUND OF THE INVENTION

(1) Field of the Invention

The present invention relates to a doze detector for detecting a doze on the basis of a degree of opening and closing of human's eyelids by the use of reflection sensors each including a pair of a light emitting element and a light receiving element. Further, the present invention relates to an alarm generating system using the doze detector.

(2) Description of Prior Art

Heretofore, a doze detector using a reflection-type photoelectric switch, as a sensor, including a pair of a light emitting element and a light receiving element has been proposed. Such a doze detector has been arranged in the following manner. The sensor is mounted on a frame of a pair of spectacles so that light is projected onto a human eye from the light emitting element of the sensor, and the reflected light from the human eye is received by the light receiving element of the sensor. At this time, the reflection point varies, that is the distance from the light emitting element varies, as a result of which the quantity of light received by the light receiving element at the opening time of the eyelids is different from that at the closing time of the same. The opening/closing of the eyelids is detected by discrimination of the level of the quantity of light reception, so that a dose is detected on the basis of the time of closure of the eyelids, and an alarm is generated by a buzzer or the like to inform the occurrence of a doze.

With such a prior art doze detector as described above, the quantity of reflected light changes as the eyeball moves even in the case where the eye is opened. There is a possibility that the light quantity may be increased to that at the closing time of the eyelids resulting in an occurrence of maldetection in detecting the condition of eyes due to the motion of the eyeball, that is, the movement of an iris.

For example, assuming that light from a light emitting element la of the detector is projected onto an area of the eye indicated by a broken line in FIG. 1 and the light reflected from the area of the eye is received by a light receiving element lb, the quantity of reflected light when the eyelids are closed is larger than that when the iris exists in actual in the area of the eye. Accordingly, the voltage level in an output of the light receiving element lb2 becomes higher as shown in FIG. 3(a) when the eyelids are closed. Thus, in the prior art doze detector, the closing of the eyelids is detected in the condition that the level voltage exceeds a predetermined threshold level $T_H$ and the occurrence of a doze is recognized by detecting the case where the eyelids are closed continuously over a predetermined period of time. Even in the case where the eyelids are opened, if the iris moves right as shown in FIG. 2, the quantity of the reflected light received by the light receiving element lb is not so different from that obtained in the case where the eyelids are closed. This is because, when the iris of the eye is in the right, the light reception area shown by the broken line is occupied by the white of the eye. On the contrary, the light reception level from the white of the eye is often higher than that obtained in the case where the eyelids are closed as shown in FIG. 3(b). Consequently, in the case where the iris of the eye is in the right, the quantity of reflected light becomes high as if the eyelids were closed. In this condition, therefore, the signal is processed in the same manner as in the condition where the eyelids are closed in spite of the fact that the eyelids are not closed, and the detector is likely to detect a doze erroneously when this condition is continued over a predetermined period of time.

In the case where car drivers use a pair of spectacles provided with such a doze detectors, the aforementioned maldetection often arises because the car drivers must move his eyeballs left and right in accordance with circumstances or in other words the iris and the whites of their eyes must move left and right. Accordingly, in this case, there may occur a problem in safe driving.

FIG. 4(a) is a waveform diagram showing the variations in the output signal of the light receiving element 1b due to the blinks and the closing of the eyes. As mentioned above and as shown in FIG. 4(a), the output signal of the light receiving element 1b of the conventional doze detector exceeds the threshold level $V_{th}$ for a relatively long period of time when the human falls into a doze b and thus the eye is closed continuously. On the other hand, upon an occurrence of blinks a and a as shown in FIG. 4(a), the output signal also exceeds the threshold level $V_{th}$ for a short time. Therefore, by detecting such a condition that the output signal exceeds the threshold $V_{th}$ continuously for the relatively long period of time, for half a second for instance, the doze detector recognizes the doze and then generates an alarm such as a buzzer or the like.

In the aforementioned conventional doze detector, the alarm is not generated until the user has fallen into a doze. As a result, a time lag arises between the point in time of initiation of a doze and the point in time of actuation of the alarm. Therefore, the conventional doze detector has a disadvantage in that accidents may happen during the time lag.

An operation of the conventional doze detector will .be- described in detail with reference to FIG. 4(b) which is a flow chart for the operation thereof. When an electric power switch of the detector is turned on, the system of the doze detector is initialized [Step (hereinafter abbreviated as "ST") 41]. The light from the light emitting element la is projected onto the eyeball, and the reflected light is received by the light receiving element lb to thereby detect a blinking condition (ST 42).

As described above, there is a difference in light intensity between the light reflected from the eyeball and the light reflected from the eyelids. This is because the distance between the eyelid and the reflection sensor is shorter than that between the eyeball and the reflection sensor, and the light reflected from the skin-color eyelid is more intensive than that reflected from the black cornea of the eye. Accordingly, a reference voltage is set in advance to be successively compared with the intensity of light (the quantity of received light) fed from the reflection sensor. For example, as shown in FIG. 4(a), in the case where the driver is in an awakening state and he does not blink, the emitted light is reflected from a portion corresponding to his eyeball including the iris so that the quantity of received light is smaller than the reference voltage that is a threshold level for a comparator 6. In this case, the eye closing time due to a blink is very short. Accordingly, upon blinking, it is detected in the ST 43 that the eye-closing time of a blink is shorter than half a second so that the operation returns to the ST 42. On the contrary, in the case where the driver falls into a doze, the eye-closing time exceeds half a second. Accordingly, in this case, the output signal having an output level higher than the threshold level is continuously produced over half a second. As the result, it is detected in the ST43 that the eye-closing time exceeds half a second, and then the operation is allowed to advance to the ST 44 where the alarm is generated for three seconds to inform the car driver of a doze state.

In the aforementioned conventional doze detector, a doze state is recognized only when an output signal having a voltage level exceeding the reference voltage is continuously produced for a predetermined period of time, over half a second for instance.

However, the state in which the driver blinks with the eye-closing time not shorter than half a second means a sleeping state in which the driver falls into a perfect doze. Accordingly, with such a conventional detector, an alarm is not generated during a drowsiness state before the driver falls into a perfect doze. Hence, it is insufficient to attain an object of the doze detector for keeping the car driver in the awakening state.

SUMMARY OF THE INVENTION

In view of the above, a primary object of the present invention is to eliminate drawbacks accompanying the prior art devices.

Another object of the present invention is to provide a doze detector capable of securely detecting the opening and closing of the eyelids regardless of the position of the iris(black) of the eye even in the case where the eyeball moves left and right, to thereby attain high precise doze detection and to produce an alarm before the user drops into a doze.

The doze detector according to the invention comprises at least two sensors each including a pair of a light emitting element and a light receiving element and a logic circuit, the sensors being provided on a support so that the light receiving element of one of the sensors is enabled to receive light reflected from the left end portion of a human eye and the light receiving element of the other sensor is enabled to receive light reflected from the opposite, right end portion of the human eye, and the respective outputs of the light receiving elements being applied to the logical circuit to be subjected to an arithmetic operation to obtain logical product (to be ANDed) by therein so that the opening and closing of the human eye is detected on the basis of the output of the logical circuit.

With such a doze detector as described above, in the condition where the iris of the eye is in the middle, the light to be received by the respective light receiving elements of the two sensors are that reflected from the respective eye portions each containing the iris(black) of the eye so that each of the output signals of the respective light receiving elements is low in level. Accordingly, the doze detector does not mistake this condition for the condition of closing of the eyelids.

On the other hand, in the case where the iris of the eye is moved to the left, one of the light receiving elements which receives the light reflected from the right area of the eye generates a high-level signal due to the white of the eye, while in the case where the black of the eye is moved to the right, one of the light receiving elements which receives the light reflected from the left area of the eye generates a high-level signal due to the white of the eye. In any case, however, the other one of the light receiving elements is low in output level. Accordingly, if the output signals of the two sensors are ANDed, the AND-output becomes low in level, so that the doze detector does not determine that the eyelids are closed. On the contrary, in the case where the eyelids are closed, the output signal level of each of the light receiving elements exceeds a predetermined threshold level. Accordingly if the output signals of the respective light receiving elements in this case are ANDed, the AND-output becomes high in level, so that the doze detector determines that the eyelids are closed. As described above, accordingly to the present invention, the condition of closure of the eyelids can be exactly detected regardless of the position of the iris to thereby attain high precise doze detection.

A second embodiment of the doze detector according to the present invention comprises: at least two sensors each including a pair of a light emitting element and a light receiving element, the sensors being provided on a support so that the light receiving element of one of the sensors is enabled to receive light reflected from the left end portion of a human eye and the light receiving element of the other sensor is enabled to receive light reflected from the opposite, right end portion of the human eye; a resistance element through which the sum of currents derived from the light receiving elements flows; comparison circuit for comparing a voltage appearing across the resistance element with a reference voltage to generate a signal when the voltage is equal to or larger than the reference voltage; and a doze discriminating circuit responsive to the output of the comparing circuit for discriminating a doze.

With such a second embodiment of a doze detector as described above, in the condition where the iris of the eye is in the middle, the light to be received by the respective light receiving elements of the two sensors is that reflected from the respective eye portion containing the iris of the eye. Thus, both the currents flowing in the respective light receiving elements are small. Accordingly, the voltage appearing across the voltage drop resistance element is lower than the reference voltage so that the comparison circuit does not generate a signal indicating the eyelids being closed. On the other hand, in the case where the iris of the eye moves to the left, a relatively large current flows in one of the light receiving element receiving light reflected from the right area (white) of the eye. Further, in the case where the iris of the eye moves to the right, a relatively large current due to the reflection from the left area (white) of the eye flows in the other light receiving element. However in any case, a current which flows through the voltage drop resistance element is not yet higher than the predetermined value. Accordingly, the voltage across the voltage drop resistance element is not yet higher than the reference voltage, so that no closed-eyelid signal, is produced by the comparing circuit.

On the contrary, in the case where the eyelids are closed, each of the light receiving elements receive the light reflected from the closed eyelids so that currents corresponding to the quantities of the reflected light flow in the respective light receiving elements. The currents are relatively large, and therefore the sum of the currents flowing through the voltage drop resistance element becomes equal to or higher than the predetermined value. Accordingly, in this case, the voltage appearing across the resistance element becomes equal to or higher than the reference voltage, as a result of which the comparison circuit produces the closed-eyelid signal. The doze detector detects the closing of the eyelids only in this case. Consequently, according to the invention, the condition of closing of the eyelids can be exactly detected regardless of the position of the black of the eye as is similar to the first embodiment.

Another embodiment of the doze detector according to the invention comprises: a sensor for detecting blinking, which includes a pair of a light emitting element and a light receiving element; a blinking interval measuring means for measuring blinking interval on the basis of an output signal of the sensor; a blinking interval extracting means for extracting an interval not shorter than a predetermined internal from the blinking intervals measured by the blinking interval measuring means; a doze judging means for recognizing an occurrence of a doze when the number of the blinking intervals extracted by the blinking interval extracting means is equal to or larger than a predetermined number in a unit time; and an alarming means for producing an alarm when the doze judging means recognizes the occurrence of a doze.

Generally, just before a man drops into a doze, it is observed that the blinking interval is prolonged. Accordingly, in the case where a predetermined number of blinking intervals each not shorter than a predetermined time are detected in a unit time, the doze detector according to the invention judges that the man begins to drop into a doze and operates the alarming means. Accordingly, a time lag between the point in time of initiation of a doze and the point in time of actuation of the alarm can be eliminated to prevent accidents from happening during the time lag.

The other embodiment of the doze detector comprises: a blink detecting means for detecting blinks; a drowsiness state detecting means for detecting blinks each having the eye-closing time equal or longer than a predetermined length from the blinks detected by the blink detecting means; a counting means for counting the number of the blinks detected by the drowsiness state detecting means; means for judging whether the number of the blinks counted by the counting means reaches a predetermined number or not; means for obtaining a period of time required for the number of the blinks counted by the counting means reaches a predetermined number; and a doze judging means for recognizing a doze state when the required time obtained by the obtaining time means is within a predetermined period of time.

The thus constructed doze detector can detect a blink having the eye-closing time of about 0.3 second when the awakening degree of the driver is lowered before he falls into a perfect doze. When the awakening degree is lowered so that a number (for example, five) of blinks are detected in one minute, the alarm is sounded to inform the driver of a risk of falling into a doze.

BRIEF DESCRIPTION OF THE DRAWINGS

In the accompanying drawings,

FIG. 3(a) and 3(b) are waveform diagrams for explaining the indiscrimination between the shut eye and the white of the eye;

FIG. 4(a) is a diagram for explaining the principle of a conventional doze detector;

FIG. 4(b) is a flow chart showing the operation of the conventional doze detector;

DESCRIPTION OF PREFERRED EMBODIMENTS

A preferred embodiment of the invention will be described more in detail.

First, the terms of "blinking", "drowsiness state" and "sleeping state" are defined as follows.

The eye-closing time in usual blinking is up to about 2 msec and the "blanking" having eye-closing time equal to or longer than 300 msec is regarded as "long blinking". In case of the number of the long blinkings exceeding a predetermined number within a predetermined period of time, it is recognized as the drowsiness state. Further, in case of the number of occurrence of blinking intervals equal to or longer than a predetermined interval exceeds a predetermined number within a predetermined period of time, it is recognized as the drowsiness state.

In the following embodiments of the present invention, it is recognized as the drowsiness state when the number of long blinks becomes equal to or larger than "5" within one minute and it is also recognized as the same when the number of occurrence of blanking intervals equal to or longer than 5 seconds becomes equal to or larger than "5" within one minute.

Figure 1:
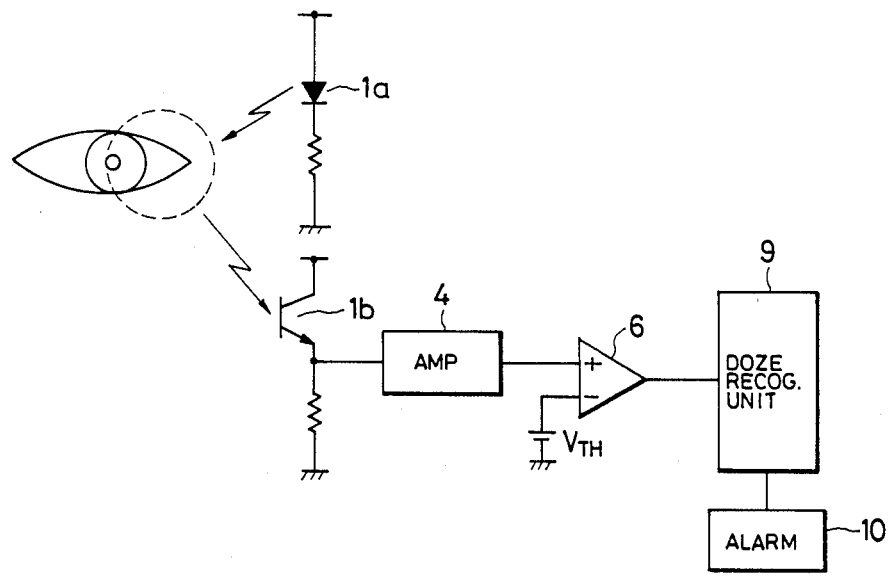
FIGS. 1 and 2 are schematic diagrams for explaining different conditions as to the position of the black or iris of the human eye according to a conventional doze detector.
Figure 2:
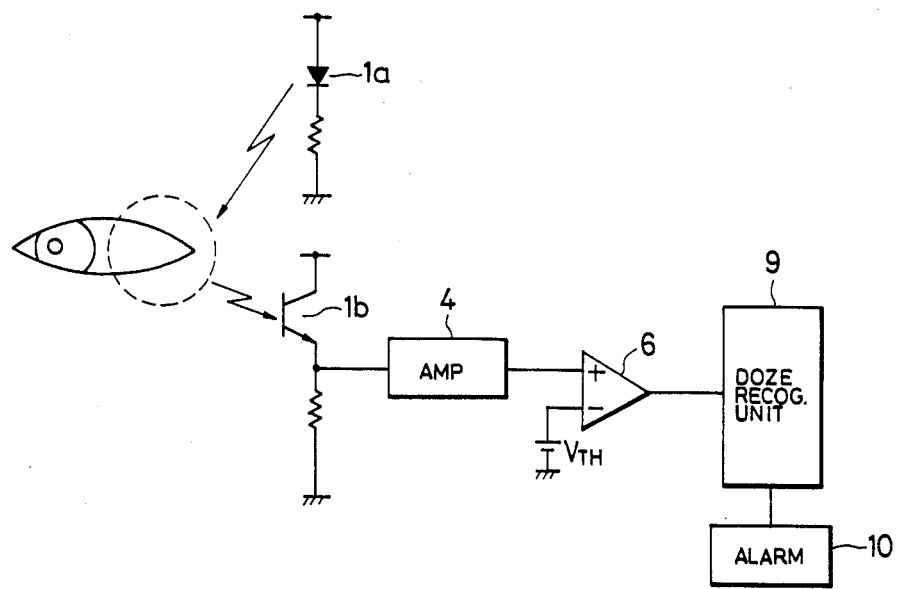
Figure 5:
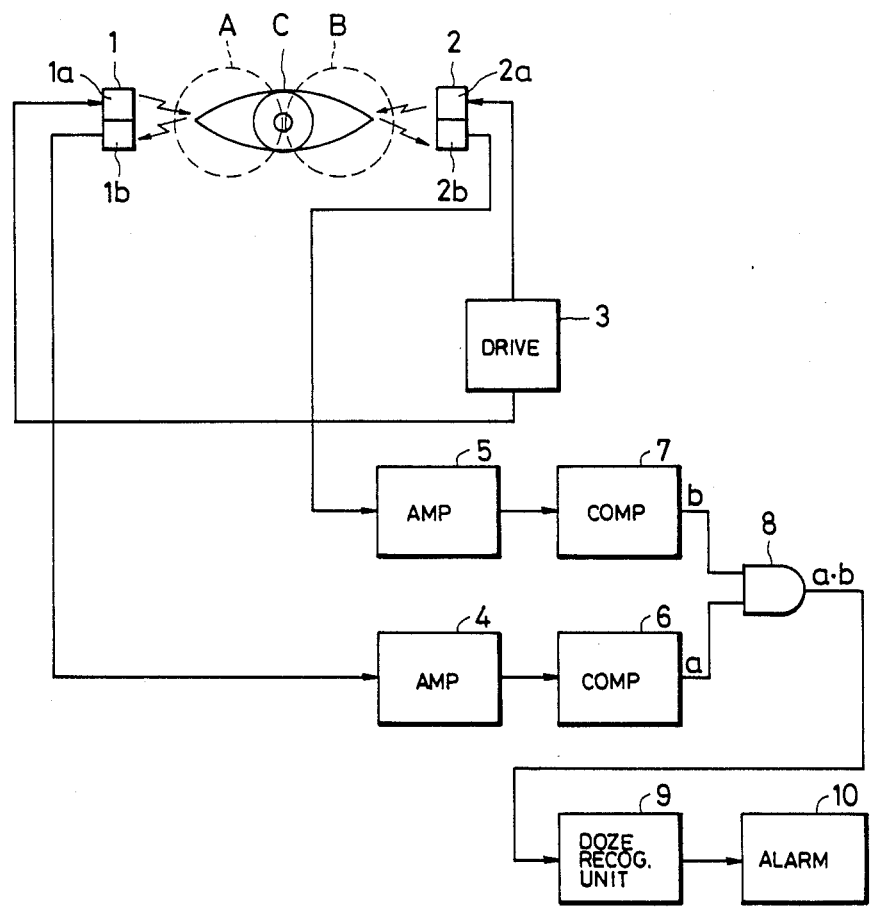
FIG. 5 is a block diagram showing a first embodiment of a doze detector according to the present invention.

FIG. 5 is a circuit block diagram showing a first embodiment of of a doze detector of the present invention.

In FIG. 5, the doze detector comprises two sensors 1 and 2. each including reflection-type photoelectric switches, respectively. The switches comprise a pair of a light emitting element 1a and a light receiving element 1b and a pair of a light emitting element 2a and a light receiving element 2b, respectively. The sensor 1 is provided on a frame of a pair of spectacles (not shown), whereas the sensor 2 is provided on a pad of the same. Light from the light emitting element 1a of the sensor 1 is projected onto a right area A of a human eye C, and the light reflected from the area A is received by the light receiving element 1b. Similarly, light from the light emitting element 2a of the sensor 2 is projected onto a left area B of the same C, and the light reflected from the area B is received by the light receiving element 2b. The light emitting elements 1a and 2a are actuated by a driving circuit 3. An output signal of the light receiving element 1b is amplified by an amplifier 4, and then the output voltage of the amplifier 4 is compared with a predetermined level in a comparator 6. The comparator 6 generates a high level signal when the output voltage of the amplifier 4 is over a predetermined level. The output of the comparator 6 is fed to one input terminal of an AND (logical product) circuit 8. Similarly, an output signal of the other light receiving element 2b is amplified in an amplifier 5 and then the output voltage of the amplifier 5 is compared with a predetermined level in a comparator 7. The comparator 7 generates a high level signal when the output voltage of the amplifier 5 is over the predetermined level. The output of the comparator 7 is fed to the other input terminal of the AND circuit 8.

In the case where both the output signals of the comparators 6 and 7 are of high, the AND circuit 8 generates a high level signal to be fed as a signal representative of the eyelids being closed to a doze discriminating circuit 9. When the eyelid-closed signal is produced continuously over a predetermined time, the doze discriminating circuit 9 recognizes an occurrence of doze and produces an output signal to actuate an alarm 10 such as a buzzer or the like.

An operation of the aforementioned doze detector will be described.

Figure 7A:
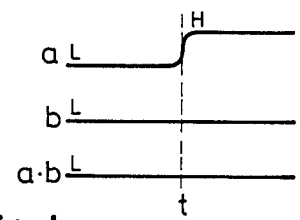
FIGS. 7(a), 7(b) and 7(c) are diagrams respectively corresponding to FIGS. 6(a), 6(b) and 6(c) to explain signal waveforms of outputs from the circuit of FIG. 5.

Assuming now that the iris of the eye C is located in the middle, the signals which are detected by the light receiving elements 1b and 2b and then amplified by the amplifiers 4 and 5, respectively are lower than the predetermined level as shown in FIG. 7(a). Accordingly, the both output signals a and b of the comparators 6 and 7 are of low level, and thus the output a*b of the AND circuit 8 is of low level.

Figure 6A:
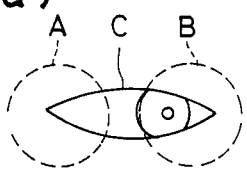
FIGS. 6(a), 6(b) and 6(c) are schematic diagrams respectively showing the position of the block or iris of a human eye and the closing condition of the eyelids.

When the iris of the eye C moves left to the area B as shown in FIG. 6(a) at a time instant t, or in other words when the area A is occupied by the white of the eye C, the output signal from the light receiving element 1b becomes a high level signal. On the other hand, the level of the output b of the comparator 7 is maintained unchanged. Accordingly, in this case, the output a*b of the AND circuit 8 is maintained lower (FIG. 6(a)).

Figure 6B:
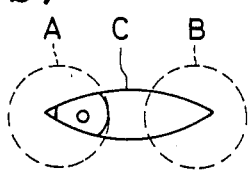
Figure 7B:
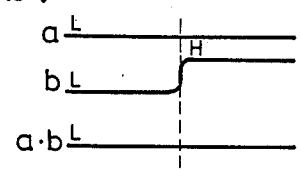
Figure 7C:
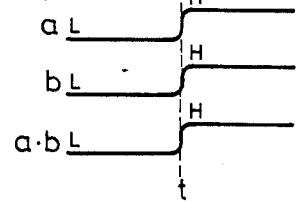

Further, when the iris of the eye C moves right to the area A as shown in FIG. 6(b), or in other words when the area B is occupied by the white of the eye C, the output signal from the light receiving element 2b becomes a high level signal b. On the other hand, the output a of the comparator 6 is maintained unchanged. Accordingly, in this case, the output a*b of the AND circuit is still in lower level as shown in FIG. 7(b)).

Figure 6C:
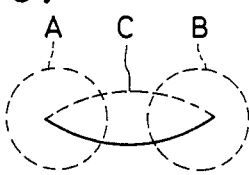

However, in the case where the eyelids of the eye C are closed as shown in FIG. 6(c), lights are reflected from both the areas A and B of the surface of the eyelid and therefore the output signals from the light receiving elements 1b and 2b become high level signals a and b. The high level signals are applied to the AND circuit 8 via the amplifiers 4 and 5 and the comparators 6 and 7 respectively. Accordingly in this case, the output a*b of the AND circuit is changed to a high level signal. to be applied to the doze discriminating circuit 9. Based on the signal, the doze discriminating circuit 9 recognizes the occurrence of a doze when the signal is continued over a predetermined time (for example: 0.5 second). Then, the alarm device is actuated to produce an alarm in response to the output of the doze discriminating circuit 9.

Figure 8:
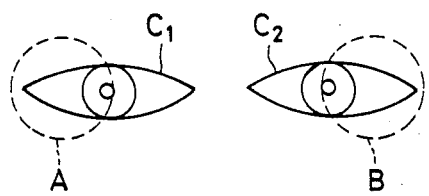
FIG. 8 is a schematic diagram showing the light receiving area of two sensors to explain a second embodiment of the present invention.

Although in the aforementioned embodiment, the sensors 1 and 2 are provided to project the light onto the right and left portions of one of human eyes C, it is a matter of course that the invention is not limited to the specific embodiment and that the invention is applicable to a modified case where the sensors 1 and 2 are provided respectively to detected reflected light from a right area A of a right eye $C_1$ and to detect the reflected light from a left area B of the other, left eye $C_2$ as shown in FIG. 8. Accordingly, in this modification, the sensor 1 is provided to a right-eye portion of the frame of a pair of spectacles whereas the sensor 2 is provided to a left-eye portion thereof.

Also in this case, the same effect as described above with reference to FIGS. 6(a) to 6(c) can be expected, because it is natural that the irises of the eyes simultaneously move left when he looks left and vice versa.

A second embodiment of the invention will be described with reference to FIGS. 9 and 10.

Figure 9:
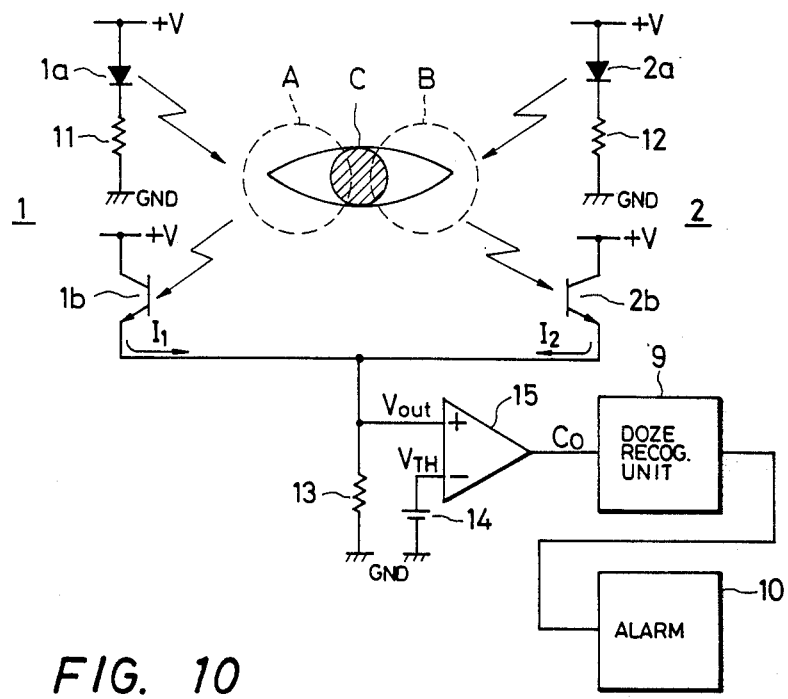
FIG. 9 is a block diagram of the second embodiment of a doze detector according to the present invention.

FIG. 9 is a circuit block diagram showing the second embodiment of the doze detector of the present invention.

In FIG. 9, elements that are the same as those in FIG. 5 bear the same or corresponding reference numerals.

The light emitting elements 1a is connected between a source voltage +V and a ground (GND) through a resistor 11 so that the light emitting element 1a emits light. Similarly, the light emitting element 2a is connected to between the source voltage +V and the ground (GND) through a resistor 12 so that the light emitting element 2a emits light. The two light receiving elements 1b and 2b are connected in parallel to each other between the source voltage +V and a common junction of the elements 1b and 2b. A resistor (that is, a voltage dropping device) 13 is connected between the common junction and the ground (GND). Further, the common junction is also connected to one input terminal (+) of the comparison circuit 15. A reference voltage from a reference voltage source 14 is applied to the other input terminal (−) of the comparison circuit 15.

When the detection voltage $V_{out}$ is higher than the reference voltage $V_{TH}$, the comparison circuit 15 generates a high-level output voltage $C_o$ the doze discriminating circuit 9. When the output voltage $C_o$ is continued over a predetermined period of time (for example: 0.5 seconds), the doze discriminating circuit 9 recognizes an occurrence of doze and produces an output to actuate the alarm 10 such as a buzzer or the like.

An operation of the aforementioned second embodiment of the doze detector will be described.

Assuming now that the iris of the eye C is located in the middle, the lights respectively emitted from the light emitting elements 1a and 2a are reflected from the areas A and B each containing a part of the iris of the eye, and then received by the light receiving elements 1b and 2b, respectively. The respective light reception currents of the light receiving elements 1b and 2b, which correspond to the quantities of the reflected light, respectively, flow in the resistor 13 so that a voltage $V_{out}$ corresponding to the sum of the currents $I_1+I_2$ flowing in the resistor 13 appears across the reSistor 13. In this case, the voltage $V_{out}$ is lower than the reference voltage $V_{TH}$. Accordingly, no output signal $C_0$ is produced from the comparison circuit 15. As a result, no alarm signal is generated from the alarm 10.

If the black iris of the eye C moves left to the area B or in other words if the area A is occupied by the white of the eye C, the current $I_1$ flowing in the light receiving element 1b receiving the light reflected from the area A becomes large, whereas the current $I_2$ flowing in the light receiving element 2b receiving the light reflected from the area B becomes very small. Accordingly, in this case, the sum of current $I_1+I_2$ which flows in the resistor 13 is substantially equal to that in the case where the black of the eye C is located in the middle. Accordingly, the voltage $V_{out}$ is still lower than the reference voltage, and thus the comparison circuit 15 does not generate the output voltage $C_o$ representing the fact that the eyelids are closed (See the period from $t_1$ to $t_2$ in FIG. 10).

Figure 10:
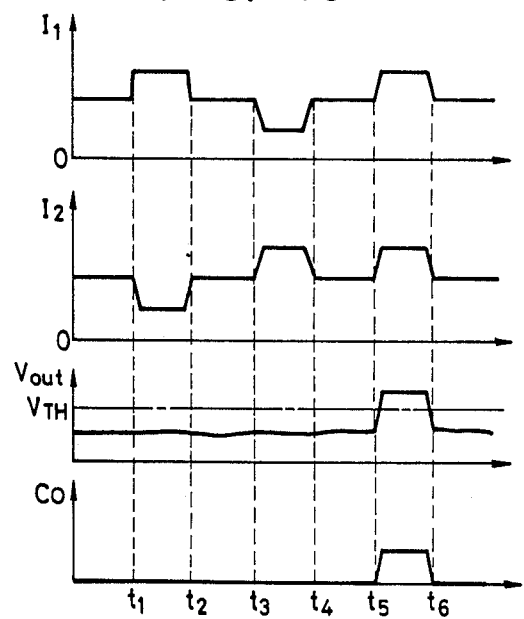
FIGS. 10 is a signal waveform time chart for explaining the operation of the second embodiment of the doze detector.

Further, if the iris of the eye C moves right to the area A or in other words if the area B is occupied by the white of the eye C, the light reception current $I_2$ flowing in the light receiving element 2b becomes large as shown in the period from $t_3$ to $t_4$ in FIG. 10. On the other hand, the light reception current $I_1$ flowing in the light receiving element 1b becomes very small, because the area A is occupied by the black of the eye. Accordingly, in this case, the sum current $I_1+I_2$ is still small. As a result, the voltage $V_{out}$ is still lower than the reference voltage. Therefore, no output voltage $C_o$ is produced from the comparison circuit 15 and no alarm signal is produced from the alarm 10.

However, in the case where the eyelids of the eye C are closed and the light is reflected from the areas A and B on the surface of the eyelids, the quantity of the reflected light is large so that the light reception currents $I_1$ and $I_2$ become large (as shown in the period from $t_5$ to $t_6$ in FIG. 10). Accordingly, the voltage $V_{out}$ across the resistor 13 exCeeds the reference voltage $V_{TH}$. As a result, the comparison circuit 15 generates the high-level output voltage $C_o$. The doze discriminating circuit 9 measures the length of time while the output $C_o$ is generated. If the length of time is equal to or longer than 0.5 seconds, the doze discriminating circuit 9 recognizes the occurrence of a doze and produces an output to actuate the alarm 10.

Figure 11:
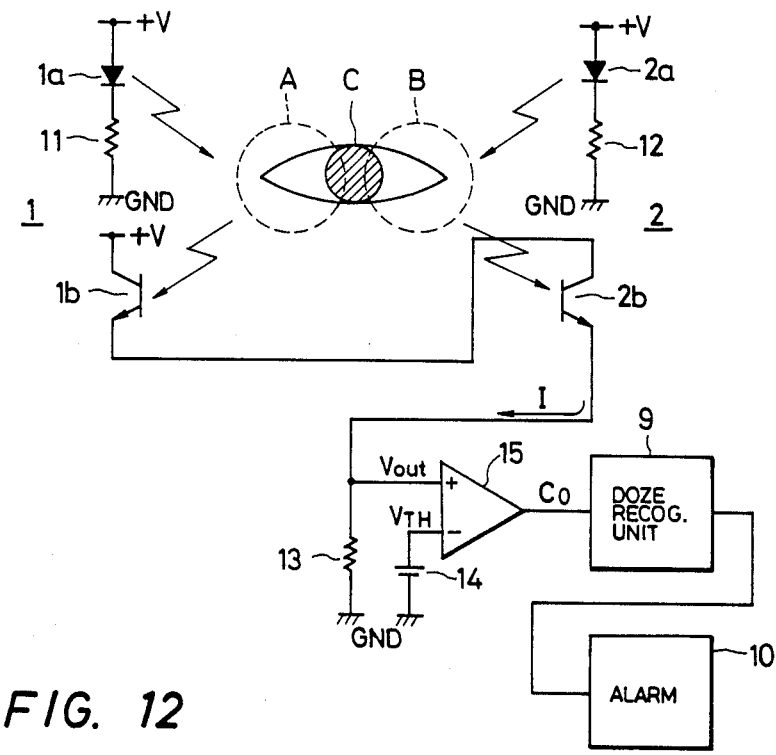
FIGS. 11 is a block diagram of a third embodiment of the doze detector according to the present invention.

FIG. 11 is a circuit diagram showing a third embodiment of a doze detector of the present invention.

The arrangement of FIG. 11 is different from that of FIG. 9 in that the light receiving elements 1b and 2b are connected in series to form a serial circuit, and that the resistor 3 is connected between the serial circuit and the ground (GND).

Figure 12:
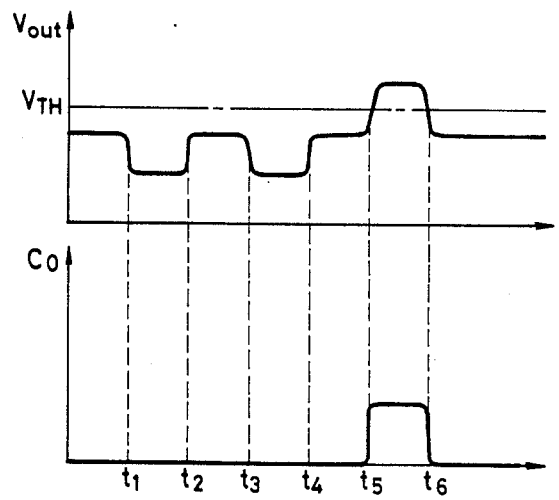
FIG. 12 is a signal waveform time chart for explaining the operation of the third embodiment of the doze detector.

Assuming now that the iris of the eye C moves left, the area B is occupied by the iris of the eye and the area A is occupied by the white of the eye. Accordingly, the light receiving element 1b receives a large quantity of reflected light, while the other light receiving element 2b receives a small quantity of reflected light. As a result, a current I flowing through the resistor 13 becomes lower than a usual current value. Thus, the voltage $V_{out}$ across the resistor 13 is lower than the reference voltage $V_{TH}$ as shown in the period from $t_1$ to $t_2$ in FIG. 12, and no output voltage $C_o$ is produced from the comparison circuit 15. On the contrary, in the case where the black of the eye C moves right, the area A is occupied by the iris of the eye and the area B is occupied by the white of the eye. As is similar to the above, the sum current I is still lower than the usual value. As a result, the voltage $V_{out}$ across the resistor 3 is lower than the reference voltage $V_{TH}$ as shown in the period from $t_3$ to $t_4$ in FIG. 12. Therefore, no output voltage $C_o$ is produced from the comparison circuit 15.

Assuming next that the eyelids are closed, both the areas A and B are covered with the eyelids. A relatively large quantity of light reflected from the eyelids is received by each of the light receiving elements 1b and 2b. The voltage drop $V_{out}$ across the resistor 3 becomes large, and exceeds the reference voltage $V_{TH}$ as shown in the period from $t_5$ to $t_6$ of FIG. 12. Accordingly, the comparing circuit 15 applies the output voltage $C_o$ to the doze discriminating circuit 9 for the period of time from $t_5$ to $t_6$. The doze discriminating circuit 9 measures the time while the output $C_o$ is applied to circuit 9. If the length of the time is over 0.5 seconds, the doze discriminating circuit 9 recognizes the occurrence of doze and produces the output to actuate the alarm 10.

It goes without saying that the same modification as that in the second embodiment is possible in the third embodiment.

Figure 13:
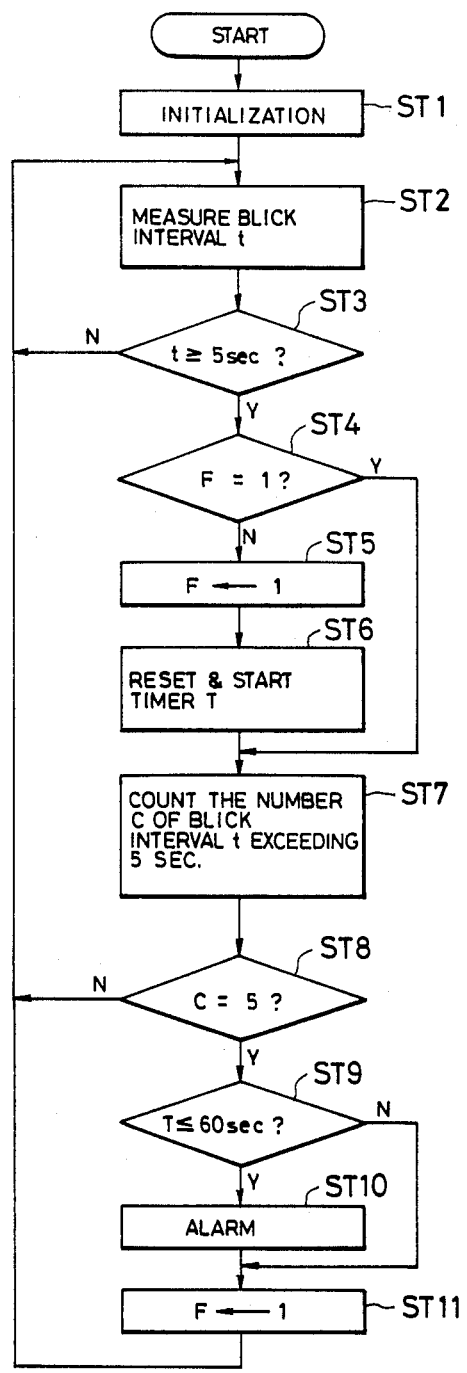
FIG. 13 is a flowchart for explaining the operation of a doze detector according to an embodiment of the present invention.

A fourth embodiment of the present invention will be described in detail with reference to FIGS. 13 through 15.

Figure 14:
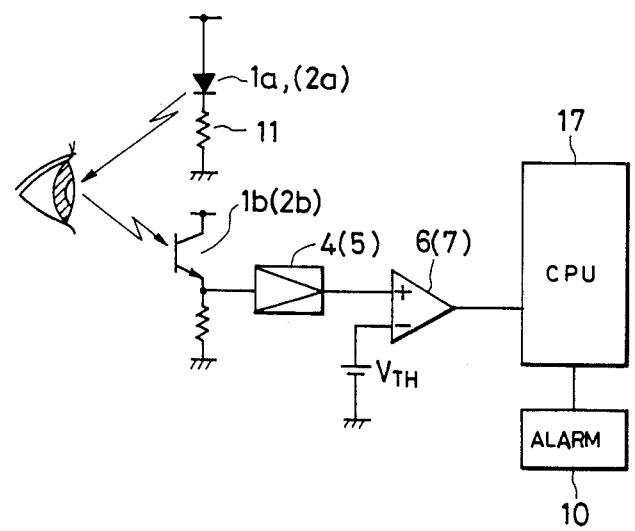
FIG. 14 is a block diagram for explaining the circuit construction of the doze detector.

FIG. 14 is a circuit block diagram of a doze detector showing the fourth embodiment of the present invention.

In FIG. 14, the output signal of the comparison circuit 6 is obtained by the same manner as those in the second and third embodiments of the present invention. Thus, the detailed description therefore is omitted intentionally. In this case, it should be noted that the output of the AND circuit 8 shown in FIG. 5 could be also used as the output signal of the comparison circuit 6.

The output of the comparison 6 is applied to a CPU (micro-computer) 7. The CPU 7 has a function of measuring blinking intervals, a function of extracting a blinking interval not shorter than a predetermined interval from the measured blinking intervals, and a function of judging whether there occurs a doze or not. The alarm 10, such as a buzzer or the like, is connected to the CPU 7 so that the alarm 8 is actuated according to the instruction of the CPU 7.

The amplifier 5, the comparator 6, the CPU 7, the alarm 8 and the like are housed in a case (not shown) connected to the frame of spectacles through lead wires (not shown).

An operation of the aforementioned fourth embodiment of the doze detector will be described with reference to FIGS. 13 to 15.

When the electric source is turned on, initialization is carried out [Step (hereinafter abbreviated as "ST") 1]. Next, a blinking interval t is measured (ST 2).

Figure 15:
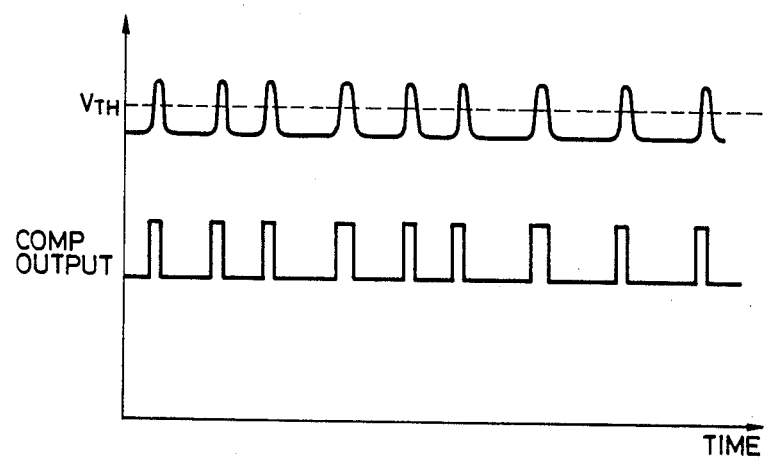
FIG. 15 is a view showing the output signals of the amplifier and the comparator of the doze detector.

FIG. 15 shows the level voltage of the light receiving element 1b(2b) amplified by the amplifier 4(5). In the case where the man blinks, his eyes are closed instantaneously. Accordingly, the output voltage of the amplifier 4(5) changes pulsewise to exceed the reference voltage $V_{th}$. At the same time, the output of the comparator 6(7) becomes high pulsewise in level, so that the CPU 17 recognizes an occurrence of blinking. Then, the CPU 17 starts measuring an interval between the high level output signal of the comparator 6(7) and the following high level output signal thereof. In other words, the CPU 17 measures a blinking interval.

In the ST 3, the CPU 7 judges whether the thus measured blinking interval t is equal to or longer than 5 seconds or not. If the judgment provides "NO", the CPU 17 recognizes that the man is in an awakening state and then allows the procedure to return to the ST 2. If the judgment provides "YES" in the ST 3, on the contrary, the procedure advances to the ST 4.

In the ST 4, the CPU 17 judges whether a flag F is "1" or not. The flag F has been set to "0" in the ST 1. Assuming now that the blinking interval t first exceeds 5 seconds, the flag is "0", and the procedure is allowed to advance to the ST 5.

In the ST 5, the flag is set to "1". In the following ST 6, a timer T for measuring a unit time is reset and started. In the ST 7, the number C of occurrence of blinking intervals t extracted, which are is equal to or longer than 5 seconds is counted.

In the ST 8, the CPU 7 judges whether the count number C reaches five. If the judgment provides "NO", the procedure returns to the ST 2 to measure another blinking interval t. As shown in FIG. 15, during shifting process from the awakening state to the doze state, that is, the drowsiness state the blinking interval t does not always exceed 5 seconds continuously. Accordingly, in the case where the judgment proves that the blinking interval t measured in the ST 2 exceeds 5 seconds in the ST 3, the procedure advances to the ST 4.

In the ST 4, the judgment provides "YES", because the flag F has been set to "1". The procedure directly jumps to the ST 7 where the number C of occurrence of the blinking intervals t equal to or longer than shorter than 5 seconds is counted. In the ST 8, in the case where the count number C is smaller than five, the procedure returns to the ST 2 in the same manner as described above.

In the ST 8, when the CPU judges that the count number C reaches five, the procedure advances to the ST 9. In the ST 9, the CPU judges whether the value of the timer T is equal to or shorter than 60 seconds or not. In the case where the judgment provides "YES", at least five blinking intervals each equal to or longer than seconds exist in 60 seconds. In this case, the CPU 17 judges that the man begins to fall into a doze, that is the CPU 17 judges the shifting from the drowsiness state to the sleeping state and the procedure advances to the ST 10 to actuate the alarm 10 for three seconds. Further, the procedure advances to the ST 11.

In the ST 11, the flag F is set to "0" and then the procedure returns to the ST 2. In short, the ST 2 establishes a new condition so that a first blinking interval t not shorter than 5 seconds can be extracted.

In the case where the judgment provides "NO" in the ST 9, that is, even if at least five blinking intervals t each equal to or longer than 5 seconds exist within a period longer than 60 seconds, the CPU judges that the man is in the awakening state and the procedure jumps to the ST 11.

As described above, according to the aforementioned fourth embodiment, the doze detector judges that the man begins to fall into a doze when the number of the blinking intervals each equal to or longer than 5 seconds is not smaller than five within 60 seconds and sounds the alarm. It is, however, to be understood that the invention as to those numerical values is not limited to the specific embodiment and that modifications are possible. For example, those numerical values may be established to be variable on the basis of external inputs.

Further, the invention may be used together with the conventional doze judging method to thereby detect a doze more securely.

In addition, it is a matter of course that the sensor used in the invention is not limited to the aforementioned reflection-type photoelectric switch and that a reflection-type ultrasonic switch may be used as the sensor.

FIG. 15 is a block diagram showing a fifth embodiment of the doze detector according to the present invention. The circuit construction is substantially same as that of the fourth embodiment shown in FIG. 14 except the provision of a memory 16.

Figure 18:
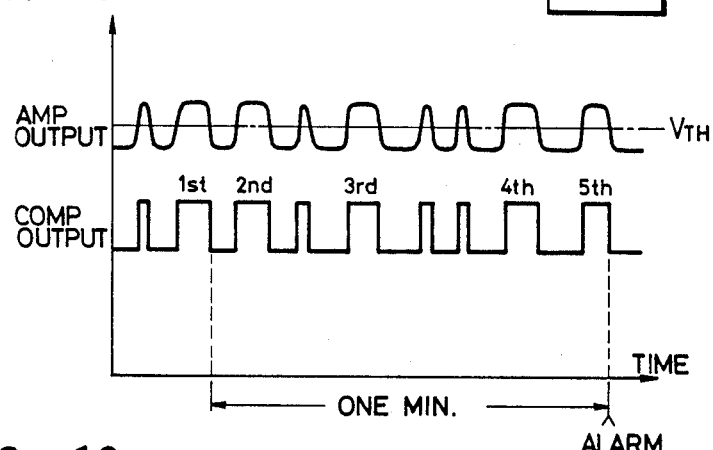
FIG. 18 is a waveform view showing the detection of the doze state by the doze detector.

In this fifth embodiment, the lowering of awakening degree is recognized by detecting increasing in the number of blinkings each having a relatively long eye-closing period of time (equal to or longer than 300 msec for instance). The CPU 17 operates to store the number of blinks each having such a relatively long eye-closing period of time into the memory 6. As shown in the waveform diagram of FIG. 18, the CPU 17 has a function of judging whether a predetermined number of blinkings having the long eye-closing period of time occur within a predetermined period of time. In this embodiment, the predetermined period of time is one minutes for instance. When the predetermined number of the blinks exist in the predetermined time (for example, on minute), the CPU 4 decides that the driver is in the drowsiness state and the driver will be in the sleeping state very soon. As a result, the CPU 17 operates to actuate the alarm 10.

Figure 16:
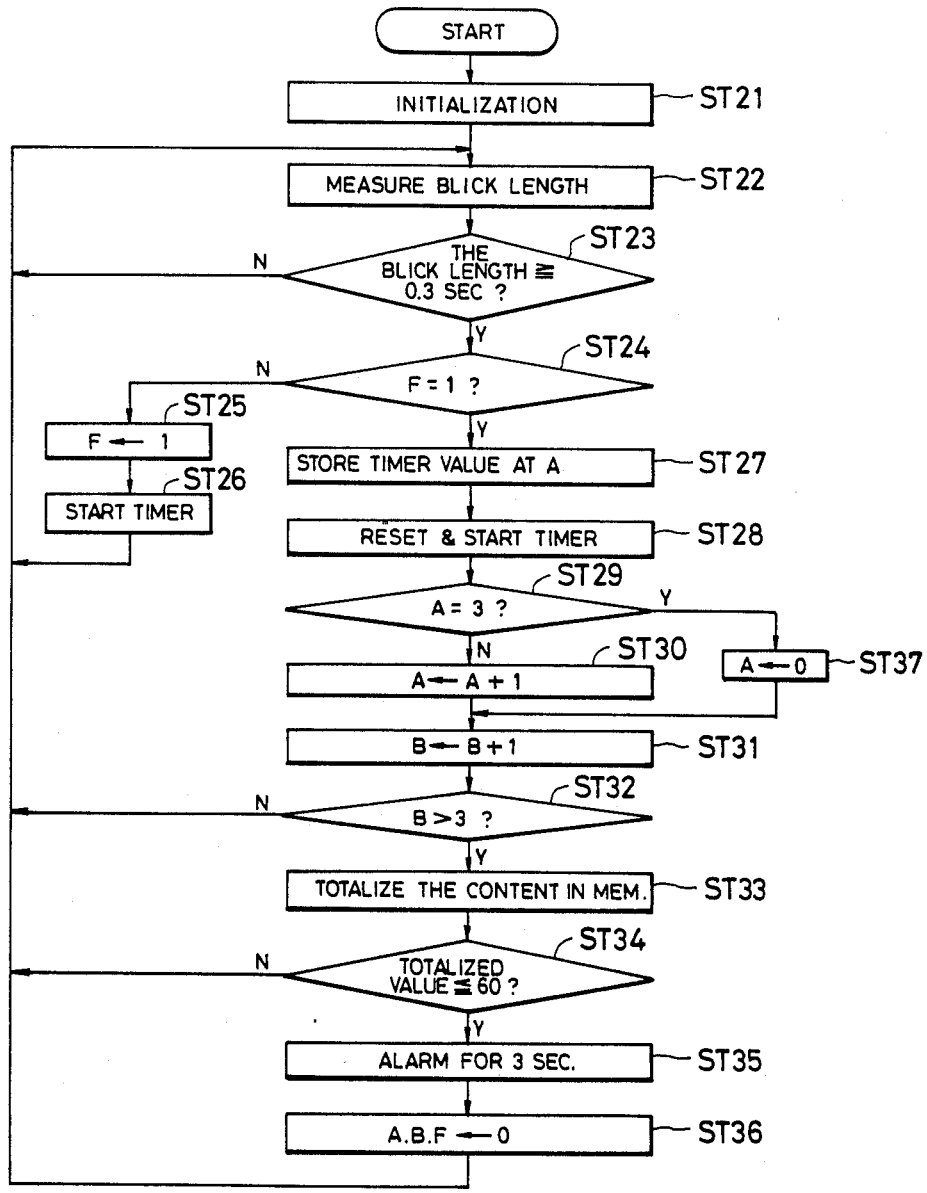
FIG. 16 is a flowchart showing the processing operation of an embodiment of the doze detector according to the present invention.
Figure 17:
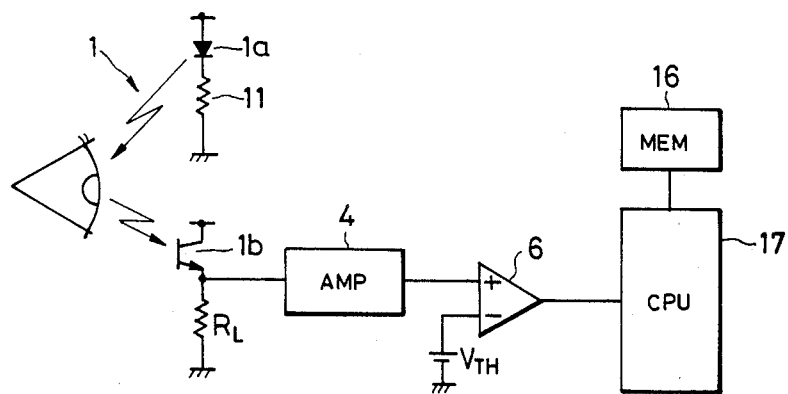
FIG. 17 is a block diagram showing an example of circuit construction of the doze detector.

FIG. 16 is a flow chart showing the operation of the fifth embodiment of the doze detector according to the present invention.

If the electric source for the instrument is turned on the instrument is initialized {Step (hereinafter abbreviated as "ST" 21], and then light is emitted from the light emitting element 1a (2a) of the reflection sensor 1 (2) to the eyeball of a driver so that his blinking condition such as the length of the eye-closing period of time in the blinking is measured in a ST 22.

In a ST 23, it is detected whether the length of the eye closing period of time in the blinking is equal to or longer than 300 msec or not. In other words, judgment is made as to whether the awaking degree is lowered and the driver is now in the drowsiness state or not. In this case, even if the light reflected from the eyelids is received so that the resulting voltage is higher than the reference voltage, the case where the eye-closing period of time is not longer than 300 msec is not recognized as the drowsiness state. That is, the CPU judges that the blinkings are normal (in the awakening state), so that the judgment in the ST 23 provides "NO" and the procedure returns to the ST 22 to continue the measurement.

Figure 19:
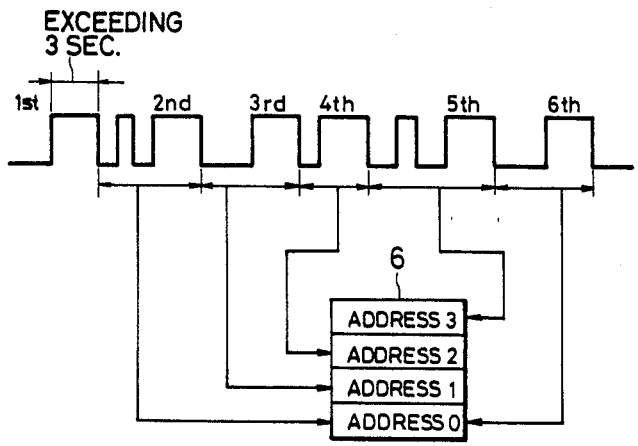
FIG. 19 is a view for explaining the condition that the number of blinks having a long eye-closing time is stored on a memory of the doze detector.

Assuming now that the awakening degree is so lowered that the eye-closing period of time is not shorter than 300 msec, the judgment in the ST 23 provides "YES" and the procedure advances to a ST 24. In the ST 24, judgment is made as to whether a flag has been set to "1" or not. In this case, since the flag has been initialized so that it is now "0", the judgment in the ST 24 provides "NO", and then the flag is set to "1" in a ST 25. At the same time, a time is started (ST 26). Then, the procedure returns to the ST 22 to detect the blinking condition. Assuming now that a second blinking with the closing period of time not shorter than 300 msec is detected, the judgment in the the ST 23 provides "YES". In this condition, the flag is "1". Accordingly, the judgment in the ST 24 provides "YES", and then the time required for detecting the second blinking is stored in the address A of the memory 6. In other words, as shown in FIG. 19, the required time is stored in the address "0" in a ST 27. Then, the timer is reset and newly started in a ST 28.

In a ST 29, it is detected whether four data of time required for the detection have been respectively stored in the four addresses of the memory 16 or not. Now only one data has been stored in the address "0" and three other addresses are not occupied. Accordingly, the judgment in the ST 29 provides "NO". Here, the address "0" is replaced by the address "1" (ST 30), and then the variable B (variable for judging whether the data have been stored in all the four addresses of the memory) is shifted from "0" to "1" (ST 31). In a ST 32, judgment is made as to whether the variable B is not smaller than "3" or not. In other words, whether data are stored in all the four addresses ("0" to "3") of the memory 16 or not. Now the variable B is "1". Accordingly, the judgment in the ST 32 provides "NO", and the procedure returns to the ST 22 to wait the detection of the next blinking having the eye-closing period of time not shorter than 300 msec. When the third blinking having the eye-closing period of time not shorter than 300 msec is detected, the judgment in the ST 23 provide "YES" and then the time required for detecting the third blinking is stored in the address "1" (ST 27). Then, the variable A is rewritten to "2" and, at the same time, the variable B is rewritten to "2" (STs 30 and 31). The aforementioned treatment is repeated in the same manner as described above till data (required time) are stored in all the four addresses ("0" to "3") of the memory or in other words till the fifth blinking is detected. Assuming now that all data are stored in the four addresses ("0" to "3"), the judgment in a ST 29 provides "YES". In this case, variable A is rewritten to "0" (ST 37), and variable B is rewritten to "4" (ST 31). In this case, the judgment in the ST 32 provides "YES", and the contents of the addresses are added. That is, data representing a total period of time required for detecting the four blinkings is obtained in the ST 33.

In a ST 34, judgment is made as to whether the total period of time is within 60 seconds or not. In other words, judgment is made as to whether the time required for detecting the fifth blinking after the detection of the second blinking is within 60 seconds or not. Assuming now that the time required exceeds 60 seconds, the judgment in the ST 34 provides "NO". Accordingly, the CPU judges that the awakening degree is not so lowered, and the procedure returns to the ST 22 to continue the detection the blinking condition. On the contrary, assuming that five blinkings each having the eye-closing period of time not shorter than 0.3 seconds are detected with in one minute, the judgment in the ST 34 provided "YES". Accordingly, the CPU judges that the awakening degree is so lowered that the driver will fall into a doze (the state of the driver is in the drowsiness state). The CPU 17 operates to actuate the alarm 10 for three seconds to produce an alarm to the driver (ST 35). Then, the variables A and B and the flag F are initialized respectively to wait for detection of the next blinking having the eye-closing period of time not shorter than 0.3 seconds. In this embodiment, even if the above-mentioned time required for the detection of the fifth blink after the detection of the first blinking is not shorter than one minute, it is a matter of course that the alarm is produced in the case where the time required for detecting the sixth blinking after the detection of the second blinking is within one minute.

Figure 21:
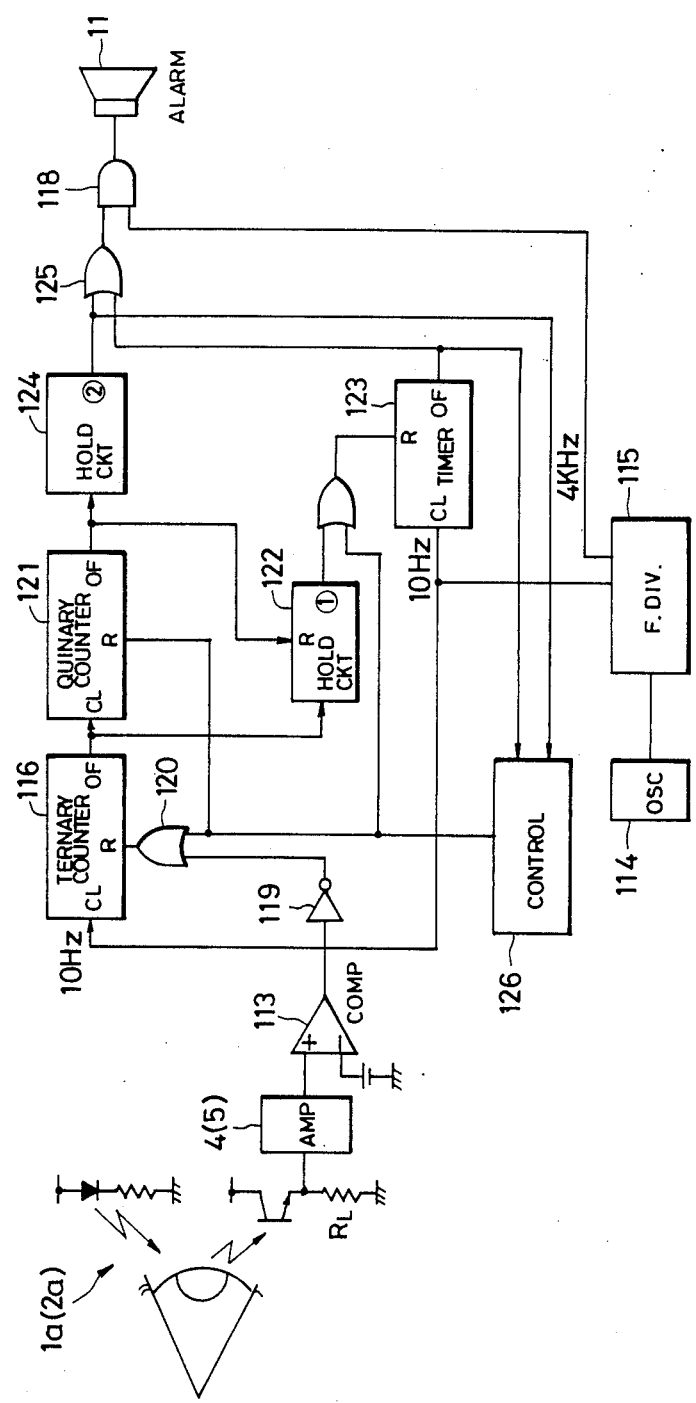
FIG. 21 is a block diagram showing an example of circuit construction of the doze detector.

FIG. 21 is circuit block diagram showing a sixth embodiment of the doze detector of the present invention.

Although the fifth embodiment is provided with the CPU 17 to perform the doze detection by using software, this sixth embodiment employs an exclusive LSI to perform the doze detection by using hardware. According to this embodiment, no memory 16 necessary to the fifth embodiment is required resulting in reducing the size of a chip and manufacturing cost thereof.

The doze detector is arranged partly in the same manner as that of the other embodiments. As is similar to the other embodiments, a high-level output signal representing the blinking is produced from is put out from the comparison circuit 113. In this embodiment, an oscillator 114 for generating a clock signal is connected to a frequency-dividing circuit 115 which generates a frequency signal of 10 Hz and another frequency signal of 4 kHz obtained by subjecting the clock signal generated from the oscillator 114 to frequency division therein. The frequency-dividing circuit 115 is connected to a ternary counter 116 as well as an AND circuit 118. The 10Hz signal is applied to the ternary counter 116, and the 4kHz signal as a sound source is supplied to the AND circuit of an alarm 117.

Figure 22:
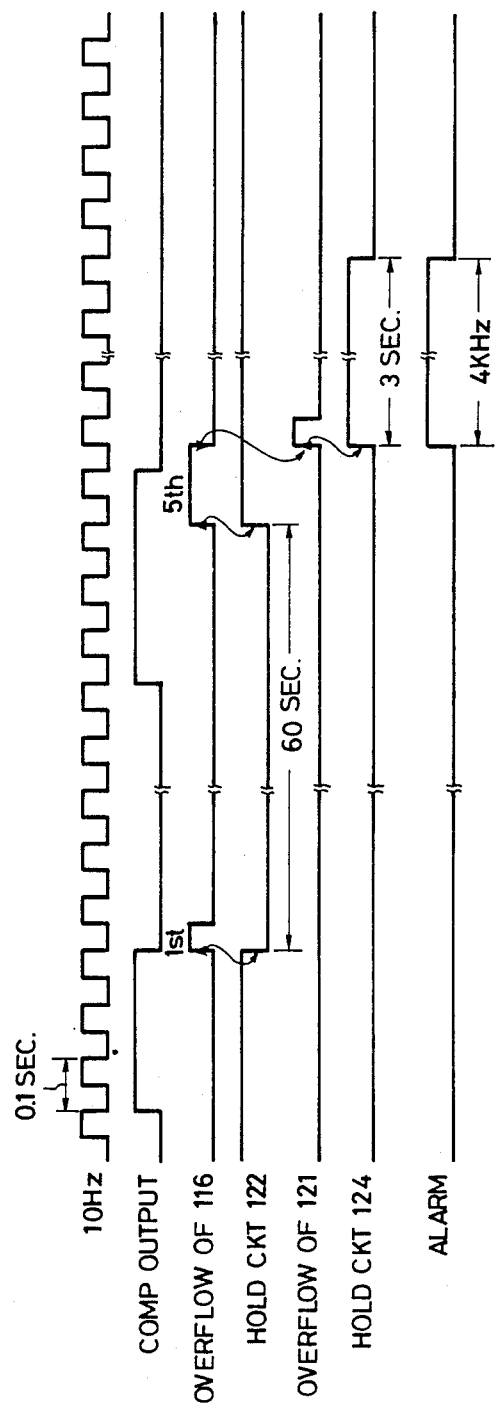
FIG. 22 is a time chart showing the detection of the doze state by the doze detector.

The comparator 113 is connected to an invertor 119 which is in turn connected to an R terminal (reset terminal) of the ternary counter 116 through an OR circuit 120. A high-level signal which is produced from the comparator 113 is inverted to a low-level signal. While the low-level signal is applied to the counter 116 continuously, the ternary counter 116 counts the 10 Hz signal. Assuming that a blinking (eye-closing time) stops after a lapse of time of 0.2 seconds, the output level of the invertor 119 is varied to a high-level at this point. Accordingly, the ternary counter 116 is reset to prevent the counter from counting up. On the contrary, if the ternary counter 116 counts the clock signal corresponding to the blinking of 0.3 seconds, the ternary counter 116 applies an overflow signal to quinary counter 121 and holds a hold circuit 122 to start a timer 123. Accordingly, the output of the hold circuit 122 becomes low as shown in FIG. 22. The low signal is applied to a reset terminal of the timer 123 to start the timer 123. When the ternary counter 116 counts the clock signal corresponding to a blinking having the eye-closing time of 300 msec, the quinary counter 121 receives the overflow signal from the counter 116. When the number of the blinks has become five, the quinary counter 121 applies an overflow signal to an other hold circuit 124 and resets the hold circuit 122 to stop the timer 123. Further, when the hold circuit 124 receives the overflow signal from the quinary counter 121, it applies an output signal to the alarm AND circuit 118 through an alarm OR circuit 125. In the case where the value of the timer 123 is within one minute, or in other words, in the case where the total time required for detection of five blinks is within 60 seconds, the alarm 117 is actuated by the hold circuit 124 so that the alarm is produced for three seconds as shown in FIG. 22.

After the alarm 117 is sounded for three seconds, a control circuit 126 generates a reset signal to initialize all the conditions of the instrument.

Figure 20:
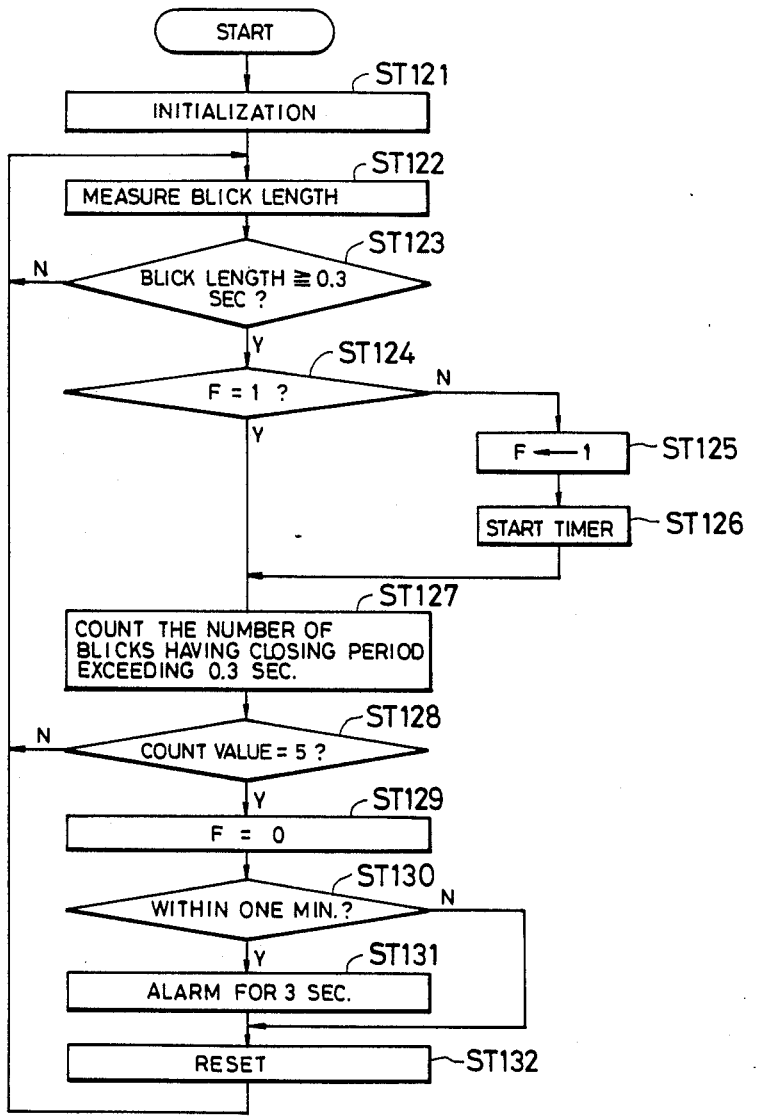
FIG. 20 is a flowchart showing the processing operation of another embodiment of the doze detector according to the present invention.

FIG. 20 is a flowchart for explaining the operation of the sixth embodiment described above.

If the electric power switch is turned on, the instrument is initialized a ST 121, and then blinking condition is measured in a ST 122. In a ST 123, judgment is made as to whether the eye-closing time of a blinking is not shorter than 0.3 second or not. In other words, judgment is made as to whether the awakening degree is so lowered that the eye-closing time of a blinking becomes not shorter than 300 msec or not. Assuming that the driver is in the awakening state so that the eye-closing time is normal, the judgment in the ST 123 provides "NO" to continue the measurement of the blinking condition. On the contrary, assuming that the awakening degree of the driver is lowered, that is the driver is in the drowsiness state so that a blinking having the eye-closing time not shorter than 300 msec is detected, the judgment in the ST 123 provides "YES" and then judgment is made as to whether the flag is "1" or not (ST 124). Because the instrument has been initialized, the flag is "0". Accordingly the flag is set to "1" (ST 125), and then the timer is started (ST 126). The number of blinks each having the eye-closing time not shorter than 300msec is counted in a ST 127. In a ST 128, judgment is made as to whether the number of the blinks is five or not. Because the number of the blinks is now one, the judgment in the ST 128 provides "NO" and the operation returns to the ST 122 to measure the blinking condition. Assuming now that the fifth blink (having the eye-closing time not shorter than 0.3 seconds) is detected in the ST 123, the clock signal corresponding to the fifth blink is counted in the ST 127. Accordingly, the judgment in the ST 128 provides "YES" and then the flag is reset to "0" (ST 129). Here, judgment is made as to whether the total time required for detecting the five blinks is within one minute or not (ST 130). Assuming that the five blinks are detected within one minute, the judgment in the ST 130 provides "YES" and then the alarm is sounded for three seconds (ST 131). Then, the timer, the blink number and the count value are reset (ST 132) and then the operation returns to the ST 122 to discriminate the blinking condition again.

As described above, according to the invention, the closing of the eyelids can be detected with high accuracy regardless of the position of the iris of the eye.Further, the doze detector according to the invention is advantageous in that it is simple in circuit arrangement and low in manufacturing cost. Moreover, according to the present invention, a drowsiness state that occurs before perfect sleeping can be detected so that an alarm to a car driver can be produced before the perfect sleeping thereby prevent an occurrence of accidents.

What is claimed is:

1. A detector for detecting blinks of an eye, comprising:

light sensing means comprising first and second light emitting elements and first and second light receiving elements, wherein the first light emitting element projects light onto one half of the eye, the second light emitting element projects light onto the other half of the eye, the first light receiving element receives a first reflected light beam from the one half of the eye, and the second light receiving element receives a second reflected light beam from the other half of the eye, said first light receiving element outputting a first output signal representative of the first reflected light beam and said second light receiving element outputting a second output signal representative of the second reflected light beam; and processing means for processing the first and second output signals so as to determine whether a blink has occurred, and for determining that a blink has occurred only when both said first output signal and said second output signal are representative of a blink;

wherein said processing means comprises means for obtaining a Boolean product of the first and second output signals, and wherein said processing means determines whether a blink has occurred using said Boolean product.

2. The detector as claimed in claim 1, further comprising doze discriminating means for discriminating a doze state in response to an output signal received from said processing means.

3. The detector as claimed in claim 2, wherein said doze discriminating means comprises:

blinking interval measuring means for measuring blinking intervals between successive blinks based on the output signal received from said processing means;

blinking interval extracting means for extracting those blinking intervals measured by said blinking interval measuring means which exceed a predetermined interval;

doze recognizing means for recognizing the doze state when the number of blinking intervals extracted by said blinking interval extracting means in a predetermined time is equal to or larger than a predetermined number; and alarm means actuated in response to an output from said doze recognizing means.

4. The detector as claimed in claim 3, wherein said predetermined interval is five seconds, said predetermined time is one minute, and said predetermined number is five.

5. The detector as claimed in claim 2, wherein said doze discriminating means comprises:

detecting means for detecting blinks which have an eye-closing time greater than a predetermined length based on the output signal received from said processing means;

counting means for counting the number of blinks detected by said detecting means;

judging means for judging whether the number of blinks counted by said counting means is equal to a predetermined number;

determining means for determining a time period required for the number of blinks counted by said counting means to be equal to the predetermined number;

doze recognizing means for recognizing the doze state when the time period is less than or equal to a predetermined time period.

6. The detector as claimed in claim 5, wherein said predetermined length is 300 msec, said predetermined number is five, and said predetermined time period is one minute.

7. A detector for detecting blinks of an eye, comprising:
light sensing means comprising first and second light emitting elements and first and second light receiving elements, wherein the first light emitting element projects light onto one half of the eye, the second light emitting element projects light onto the other half of the eye, the first light receiving element receives a first reflected light beam from the one half of the eye, and the second light receiving element receives a second reflected light beam from the other half of the eye, said first light receiving element outputting a first output signal representative of the first reflected light beam and said second light receiving element outputting a second output signal representative of the second reflected light beam; and
processing means for processing the first and second output signals so as to determine whether a blink has occurred, and for determining that a blink has occurred only when both said first output signal and said second output signal are representative of a blink;
wherein said processing means comprises means for determining the sum of the first and second output signals, and wherein said processing means determines whether a blink has occurred using said sum.

8. The detector as claimed in claim 7, further comprising doze discriminating means for discriminating a doze state in response to an output signal received from said processing means.

9. The detector as claimed in claim 8, wherein said doze discriminating means comprises:
blinking interval measuring means for measuring blinking intervals between successive blinks based on the output signal received from said processing means;
blinking interval extracting means for extracting those blinking intervals measured by said blinking interval measuring means which exceed a predetermined interval;
doze recognized means for recognizing the dose state when the number of blinking intervals extracted by said blinking interval extracting means in a predetermined time is equal to or larger than a predetermined number; and
alarm means actuated in response to an output from said doze recognizing means.

10. The detector as claimed in claim 9, wherein said predetermined interval is five seconds, said predetermined time is one minute, and said predetermined number is five.

11. The detector as claimed in claim 8, wherein said doze discriminating means comprises:
detecting means for detecting blinks which have an eye-closing time greater than a predetermined length based on the output signal received from said processing means;
counting means for counting the number of blinks detected by said detecting means;

judging means for judging whether the number of blinks counted by said counting means is equal to a predetermined number;
determining means for determining a time period required for the number of blinks counted by said counting means to be equal to the predetermined number;
doze recognizing means for recognizing the doze state when the time period is less than or equal to a predetermined time period.

12. The detector as claimed in claim 11, wherein said predetermined length is 300 msec, said predetermined number is five, and said predetermined time period is one minute.

13. A method for detecting blinks of an eye, comprising:
projecting a first light beam onto one half of the eye and a second light beam onto the other half of the eye;
receiving a first reflected light beam from the one half of the eye and a second reflected light beam from the other half of the eye;
outputting a first output signal representative of the first reflected light beam and a second output signal representative of the second reflected light beam; and
determining whether a blink has occurred using said first and second output signals, wherein a blink is determined to have occurred only when both said first output signal and said second output signal are representative of a blink;
wherein said determining step includes obtaining a Boolean product of the first and second output signals, and wherein said Boolean product is used to determine whether a blink has occurred.

14. The method as claimed in claim 13, further comprising the step of discriminating a doze state upon determining blinks.

15. The method as claimed in claim 14, wherein said doze discriminating step comprises:
measuring blinking intervals between successive blinks determined by said blink determining step;
extracting those blinking intervals measured in said blinking interval measuring step which exceed a predetermined interval;
recognizing the doze state when the number of blinking intervals extracted in said blinking interval extracting step in a predetermined time is equal to or larger than a predetermined number; and
actuating an alarm when the doze state is recognized.

16. The method as claimed in claim 15, wherein said predetermined interval is five seconds, said predetermined time is one minute, and said predetermined number is five.

17. The method as claimed in claim 14, wherein said doze discriminating step comprises:
detecting which blinks determined by said blink determining step have an eye-closing time greater than a predetermining length;
counting the number of blinks detected in said detecting step;
judging whether the number of blinks counted in said counting step is equal to a predetermined number;
determining a time period required for the number of blinks counted in said counting step to be equal to the predetermined number;
recognizing the doze state when the time period is less than or equal to a predetermined time period.

18. The method as claimed in claim 17, wherein said predetermined length is 300 msec, said predetermined number is five, and said predetermined time period is one minute.

19. A method for detecting blinks of an eye, comprising:
projecting a first light beam onto one half of the eye and a second light beam onto the other half of the eye;
receiving a first reflected light beam from one half of the eye and a second reflected light beam from the other half of the eye;
outputting a first output signal representative of the first reflected light beam and a second output signal representative of the second reflected light beam; and
determining whether a blink has occurred using said first and second output signals, wherein a blink is determined to have occurred only when both said first output signal and said second output signal are representative of a blink;
wherein said determining step includes calculating the sum of the first and second output signals, and wherein said sum is used to determine whether a blink has occurred.

20. The method as claimed in claim 19, further comprising the step of discriminating a doze state upon determining blinks.

21. The method as claimed in claim 20, wherein said doze discriminating step comprises:
measuring blinking intervals between successive blinks determined by said blink determining step;
extracting those blinking intervals measured in said blinking interval measuring step which exceed a predetermined interval;
recognizing the doze state when the number of blinking intervals extracted in said blinking interval extracting step in a predetermined time is equal to or larger than a predetermined number; and
actuating an alarm when the doze state is recognized.

22. The method as claimed in claim 21, wherein said predetermined interval is five seconds, said predetermined time is one minute, and said predetermined number is five.

23. The method as claimed in claim 20, wherein said doze discriminating step comprises:
detecting which blinks determined by said blink determining step have an eye-closing time greater than a predetermined length;
counting the number of blinks detected in said detecting step;
judging whether the number of blinks counted in said counting step is equal to a predetermined number;
determining a time period required for the number of blinks counted in said counting step to be equal to the predetermined number;
recognizing the doze state when the time period is less than or equal to a predetermined time period.

24. The method as claimed in claim 23, wherein said predetermined length is 300 msec, said predetermined number is five, and said predetermined time period is one minute.

* * * * *